(12) United States Patent
Oakley (10) Patent No.: US 8,263,372 B2
(45) Date of Patent: Sep. 11, 2012

(54) CARBON CAPTURE IN FERMENTATION (75) Inventor: Simon David Oakley, Parnell (NZ)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

(21) Appl. No.: 13/058,678

(22) PCT Filed: Apr. 29, 2010

(86) PCT No.: PCT/NZ2010/000082
§ 371 (c)(1),
(2), (4) Date: Aug. 3, 2011

(87) PCT Pub. No.: WO2010/126382
PCT Pub. Date: Nov. 4, 2010

(65) Prior Publication Data
US 2012/0052541 A1 Mar. 1, 2012

Related U.S. Application Data (60) Provisional application No. 61/173,968, filed on Apr. 29, 2009.

(51) Int. Cl.
C12P 7/24 (2006.01)
C12P 7/54 (2006.01)
C12P 7/06 (2006.01)
C12P 1/04 (2006.01)
C12M 1/00 (2006.01)

(52) U.S. Cl. ........ 435/136; 435/140; 435/161; 435/170; 435/289.1

(58) Field of Classification Search .................. 435/136, 435/140, 161, 170, 289.1
See application file for complete search history.

(56) References Cited

U.S. PATENT DOCUMENTS

| 5,173,429 A | 12/1992 | Gaddy et al. |
| 5,593,886 A | 1/1997 | Gaddy |
| 5,807,722 A | 9/1998 | Gaddy |
| 5,821,111 A | 10/1998 | Grady et al. |
| 6,136,577 A | 10/2000 | Gaddy |
| 6,340,581 B1 | 1/2002 | Gaddy |
| 6,368,819 B1 | 4/2002 | Gaddy et al. |
| 6,753,170 B2 | 6/2004 | Gaddy et al. |
| RE39,175 E | 7/2006 | Gaddy et al. |
| 7,196,218 B2 | 3/2007 | Gaddy et al. |
| 7,285,402 B2 | 10/2007 | Gaddy et al. |
| 2008/0166790 A1* | 7/2008 | Day ........................ 435/262.5 |

FOREIGN PATENT DOCUMENTS

| WO | 2008/028055 | 3/2008 |
| WO | 2008/154301 | 12/2008 |
| WO | 2009/020747 | 2/2009 |

(Continued)

OTHER PUBLICATIONS

Phillips, J.R., et al. "Synthesis Gas as Substrate for the Biological Production of Fuels and Chemicals." Applied Biochemistry and Biotechnology, 1994, 45/46. pp. 145-157.

(Continued)

Primary Examiner — Rosanne Kosson
(74) Attorney, Agent, or Firm — Frank S. Molinaro (57) ABSTRACT The present invention relates to improvement in efficiency in gasification for use with syngas fermentation. In particular, the invention relates to increasing the overall carbon capture efficiency of a gasification/fermentation process to produce products such as alcohols.

13 Claims, 2 Drawing Sheets

FOREIGN PATENT DOCUMENTS

WO 2009/058028 5/2009

OTHER PUBLICATIONS

Abrini J. et al. "*Clostridium autoethanogenum*, sp. Nov., an Anaerobic Bacterium that Produces Ethanol from Carbon Monoxide", Archives of Microbiology. 1994, vol. 161, pp. 345-351.

Ragsdale, S.W. "Life with Carbon Monoxide." Critical Reviews in Biochemistry and Molecular Biology, 2004, 39, pp. 165-195.

Henstra, et al. "Microbiology of Synthesis Gas Fermentation for Biofuel Production." Current Opinion in Biotechnology, 2007, 18, pp. 200-206.

* cited by examiner

CARBON CAPTURE IN FERMENTATION

CROSS REFERENCE TO RELATED APPLICATIONS

This application is a National Stage of International Application No. PCT/NZ2010/000082, filed on Apr. 29, 2010, which claims the benefit of the priority date of U.S. Provisional Application No. 61/173,968, filed Apr. 29, 2009. The content of the prior application mentioned above is incorporated herein by reference.

FIELD OF THE INVENTION

This invention relates to systems and methods for improving overall carbon capture and/or improving overall efficiency in processes including microbial fermentation. In particular, the invention relates to improving carbon capture and/or improving efficiency in processes including microbial fermentation of a syngas substrate comprising CO.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major, low cost, energy-rich by-product of the incomplete combustion of organic materials such as coal or oil and oil derived products. For example, the steel industry in Australia is reported to produce and release into the atmosphere over 500,000 tonnes of CO annually. Additionally or alternatively, CO rich gas streams (syngas) can be produced by gasification of carbonaceous materials, such as coal, petroleum and biomass. Carbonaceous materials can be converted into gas products including CO, CO2, H2 and lesser amounts of CH4 by gasification using a variety of methods, including pyrolysis, tar cracking and char gasification. Syngas can also be produced in a steam reformation process, such as the steam reformation of methane or natural gas.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is typically associated with co-production of acetate and/or acetic acid. As some of the available carbon is typically converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

WO2007/117157 and WO2008/115080, the disclosure of which are incorporated herein by reference, describe processes that produce alcohols, particularly ethanol, by anaerobic fermentation of gases containing carbon monoxide. Acetate produced as a by-product of the fermentation process described in WO2007/117157 is converted into hydrogen gas and carbon dioxide gas, either or both of which may be used in the anaerobic fermentation process.

The fermentation of gaseous substrates comprising CO, to produce products such as acids and alcohols, typically favours acid production. Alcohol productivity can be enhanced by methods known in the art, such as methods described in WO2007/117157, WO2008/115080, WO2009/022925 and WO2009/064200, which are fully incorporated herein by reference.

U.S. Pat. No. 7,078,201 and WO 02/08438 also describe improving fermentation processes for producing ethanol by varying conditions (e.g. pH and redox potential) of the liquid nutrient medium in which the fermentation is performed. As disclosed in those publications, similar processes may be used to produce other alcohols, such as butanol.

Microbial fermentation of CO in the presence of $H_2$ can lead to substantially complete carbon transfer into an alcohol. However, in the absence of sufficient $H_2$, some of the CO is converted into alcohol, while a significant portion is converted to $CO_2$ as shown in the following equations:

$$6CO + 3H_2O \rightarrow C_2H_5OH + 4CO_2$$

$$12H_2 + 4CO_2 \rightarrow 2C_2H_5OH + 6H_2O$$

The production of $CO_2$ represents inefficiency in overall carbon capture and if released, also has the potential to contribute to Green House Gas emissions. Furthermore, carbon dioxide and other carbon containing compounds, such as methane, produced during a gasification process may also be released into the atmosphere if they are not consumed in an integrated fermentation reaction.

It is an object of the present invention to provide system(s) and/or method(s) that overcomes disadvantages known in the art and provides the public with new methods for the optimal production of a variety of useful products.

SUMMARY OF THE INVENTION

In a first aspect, the invention provides a method of increasing carbon capture in a fermentation process, the method including gasification of a feedstock to produce a syngas substrate in a gasifier then contacting at least a portion of the syngas substrate with one or more micro-organisms to produce one or more products in a bioreactor, wherein an exit stream exits the bioreactor and wherein at least a portion of the exit stream is directed into the gasifier.

In particular embodiments, the exit stream comprises one or more components of the syngas stream not converted to products and/or by-products by fermentation. In another embodiment, the exit stream comprises gaseous by-products produced during fermentation of the substrate.

In particular embodiments, components of the syngas stream not converted to products and/or by-products of the fermentation include CO, CO2, CH4, and/or H2. In certain embodiments, at least a portion of the CO2 produced as a by-product of fermentation is returned to the gasifier.

In some embodiments of the invention, the method includes separating and/or enriching at least a portion of selected components of the exit stream and returning the separated and/or enriched components to the gasifier. In particular embodiments, CO2 and/or CH4 are separated and/or enriched and returned to the gasifier.

In another embodiment, the separated and/or enriched components are returned to the bioreactor. In particular embodiments, CO and/or H2 are separated and/or enriched and returned to the bioreactor.

In yet another embodiment, the method includes separating at least a portion of one or more fermentation products from the exit stream before at least a portion of the exit stream is passed to the gasifier. In particular embodiments, the product is alcohol. In particular embodiments, ethanol is removed from the exit stream before at least a portion of the exit stream is returned to the gasifier.

In a second aspect, the invention provides a method of improving overall efficiency and/or carbon capture of a fermentation process, the process including:
conversion of a feedstock to syngas in a gasifier;
passing at least a portion of the syngas to a bioreactor;
fermenting at least a portion of the syngas in the bioreactor to produce products;
wherein the method includes separating at least a portion of one or more components of the syngas prior to passing the syngas to the bioreactor, and diverting the one or more components to the gasifier.

In particular embodiments one or more components separated from the syngas stream are selected from H2S, CO2, tars and/or BTEX.

In a third aspect the invention provides a method of producing products by fermentation of a syngas substrate by one or more microorganisms, wherein the syngas is produced in a gasifier, the method including directing at least a portion of a carbon dioxide by-product produced in the fermentation, into the gasifier.

In particular embodiments of the various preceding aspects, the anaerobic fermentation produces products including acid(s) and alcohol(s) from CO and optionally H2. In particular embodiments, the anaerobic fermentation is conducted in a bioreactor, wherein one or more microbial cultures convert CO and optionally H2 to products including acid(s) and/or alcohol(s). In certain embodiments, the product is ethanol.

In particular embodiments, the microbial culture is a culture of carboxydotrophic bacteria. In certain embodiments, the bacteria is selected from *Clostridium, Moorella* and *Carboxydothermus*. In particular embodiments, the bacterium is *Clostridium autoethanogenum*.

According to various embodiments of the invention, the carbon source for the fermentation reaction is syngas derived from gasification. The syngas substrate will typically contain a major proportion of CO, such as at least about 20% to about 95% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when significant amounts of $H_2$ and optionally $CO_2$ are present.

According to a fourth aspect, the invention provides a system for increasing the efficiency of processes of producing products by microbial fermentation of syngas substrates, the system comprising:
1) a gasifier configured to produce a syngas stream comprising CO and H2;
2) a bioreactor configured to convert at least a portion of CO and optionally H2 from the syngas stream to products;
3) means for passing at least one component of the syngas stream not converted to product(s) and/or at least one by-product of the fermentation from an exit stream exiting the bioreactor back to the gasifier.

In particular embodiments, the system includes means to separate and/or enrich selected components from the exit stream and pass them back to the gasifier. In particular embodiments, the system includes means to separate and/or enrich at least a portion of CO2 and/or CH4 from the exit stream and pass the separated and/or enriched CO2 and/or CH4 back to the gasifier.

In certain embodiments, the system further includes means to separate and/or enrich at least a portion of CO and/or H2 from the exit stream and pass the separated and/or enriched CO and/or H2 back to the bioreactor.

In another embodiment, the system further includes means to separate and/or enrich one or more products in the exit stream.

According to a fifth aspect, the invention provides a system for increasing the efficiency of processes of producing products by microbial fermentation of syngas substrates, the system comprising:

1) a gasifier configured to produce a syngas stream comprising CO and H2;
2) means for separating at least a portion of selected components from the syngas stream and passing the separated components back to the gasifier;
3) means for passing a remainder of the syngas stream comprising CO and H2 to a bioreactor
4) a bioreactor configured to convert at least a portion of CO and optionally H2 from the remainder of the syngas stream to products.

In particular embodiments, the system includes means to separate and/or enrich at least a portion of H2S, CO2, tars and/or BTEX from the syngas substrate stream prior to passing to the bioreactor.

In particular embodiments of the forth and fifth aspects, the system comprises means for determining whether the syngas substrate stream comprising CO and H2 has a desired composition. Any known means may be used for this purpose. Additionally or alternatively, determining means are provided to determine the composition of the exit stream and/or the separated stream before it is returned to the gasifier. If it is determined the stream(s) have an undesirable composition for a particular stage, the stream can be diverted elsewhere.

In particular embodiments of the invention, the system includes means for heating and/or cooling the various streams passed between various stages of the system.

Additionally or alternatively, the system includes means for compressing at least portions of the various streams passed between various stages of the system.

According to particular embodiments of each of the various aspects of the invention, the process used for gas separation and/or enrichment comprises one or more of cryogenic fractionation, molecular adsorption, pressure swing adsorption or absorption Although the invention is broadly as defined above, it is not limited thereto and also includes embodiments of which the following description provides examples.

BRIEF DESCRIPTION OF THE DRAWINGS

The invention will now be described in detail with reference to the accompanying Figures in which.

DETAILED DESCRIPTION OF THE INVENTION

Syngas, produced from the gasification of carbonaceous materials, such as coal, petroleum, biofuel or biomass can be anaerobically fermented to produce products, such as acids and alcohols. Syngas derived substrates suitable for use in fermentation processes typically also contain $CO_2$ and other carbon containing compounds such as methane. In addition, in many fermentation reactions, for example where CO is converted to products including acids and/or alcohols, significant volumes of $CO_2$ can be produced. The present invention relates to methods, systems, and processes to improve the overall carbon capture in such fermentation processes utilising syngas derived from gasification.

In accordance with the methods of the invention, overall efficiency and/or carbon capture of a fermentation process of a syngas substrate, derived from gasification, is improved.

According to a particular broad aspect, there is provided a method of improving overall efficiency and/or carbon capture of a fermentation process, the method including:
conversion of a feedstock to syngas in a gasifier;
passing the syngas to a bioreactor;
fermenting at least a portion of the syngas in the bioreactor to produce products;
wherein at least one component of the syngas not converted to products and/or by-products of the fermentation process, exit the bioreactor in an exit stream, wherein at least a portion of the exit stream is returned to the gasifier.

In particular embodiments, carbon containing syngas components produced by gasification, such as CO, CO2 and/or CH4, are passed to a bioreactor, wherein at least a portion of the CO is converted to products, such as alcohols and/or acids, by one or more carboxydotrophic bacteria. Components not converted into products, typically exit the bioreactor in an exit stream. However, in accordance with the invention, the carbon containing components in the exit stream, such as unconverted CO, CO2 and/or CH4 can be redirected back to the gasifier and at least partially recycled into compounds including CO, CO2 and CH4. Other non carbon containing components, such as H2 and/or H2O exiting the bioreactor in the exit stream can also be passed back to the gasifier and recycled.

Without wishing to be bound by theory it is considered that in a gasifier, carbonaceous material undergoes several different processes. Essentially, a limited amount of oxygen or air is introduced into the gasifier to allow some of the organic material to be burned to produce carbon monoxide and energy. This in turn, drives a second reaction that converts further organic material to hydrogen and additional carbon monoxide. Gasifiers operating under steady state conditions produce gas streams containing components including CO, CO2, H2 and optionally CH4 in substantially constant proportions. Thus, returning carbon containing components, such as unconverted CO, CO2 and/or CH4, back to the gasifier, will reduce the amount of fuel required to be gasified to produce the same substantially constant stream. In turn, the CO, CO2 and/or CH4 in the gasified stream can be passed to the bioreactor, wherein further CO and optionally CO2 will be converted to products, thus improving overall carbon capture of the process.

Furthermore, hydrogen containing components, such as H2 remaining after fermentation, water and/or products stripped from the bioreactor by the gas stream can also be recycled back to the gasifier, thus improving the overall H2 capture of the process. Additionally or alternatively, increasing efficiency of hydrogen provision to the bioreactor will also improve overall carbon capture, as H2 reduces the amount of CO2 produced in the fermentation reaction.

In particular embodiments, desired components, such as products stripped from the bioreactor are separated from the exit stream. The separated product(s) can be combined with product(s) separated from the fermentation broth by conventional means.

In another embodiment of the invention, the exit gas exiting the fermentation reaction can optionally undergo separation to remove desirable components, such as CO and/or H2 and return them directly to the bioreactor. Additionally, or alternatively, gas separation can be used to enrich a particular component of the exit stream, such as CO2 and/or CH4, such that the enriched CO2 and/or CH4 stream can be passed to the gasifier. In particular embodiments, a first component of the exit stream, such as CO2 or CH4, can be separated from one or more second components. In particular embodiments, the first component is returned to the gasifier, whereas one or more second components can be directed to the bioreactor and/or a waste port. Other less desirable components, for example inert compounds such as N2, can also be separated by means known in the art and diverted to a waste stream for disposal.

Improvements in fermentation efficiency observed through increases in ethanol productivity wherein CO2 is provided to a gasifier are known in the art. The optimum amounts of CO2 provided to the gasifier are detailed in WO2009/154788 which is fully incorporated herein by reference.

DEFINITIONS

Unless otherwise defined, the following terms as used throughout this specification are defined as follows:

The terms "carbon capture" and "overall carbon capture" relate to the efficiency of conversion of a carbon source, such as a feedstock, into products. For example, the amount of carbon in a woody biomass feedstock converted into useful products, such as alcohol.

The term "feedstock" refers to carbonaceous material such as municipal solid waste, forestry material, wood waste, construction material, vegetative material, coal, oil, pulp and paper waste materials for example black liquor, petrochemical co-products, biogas, tyres and combinations thereof.

The term "syngas" refers to a gas mixture that contains at least a portion of carbon monoxide and hydrogen produced by gasification and/or reformation of a carbonaceous feedstock.

The term "substrate comprising carbon monoxide" and like terms should be understood to include any substrate in which carbon monoxide is available to one or more strains of bacteria for growth and/or fermentation, for example.

"Gaseous substrates comprising carbon monoxide" include any gas which contains carbon monoxide. The gaseous substrate will typically contain a significant proportion of CO, preferably at least about 5% to about 95% CO by volume.

The term "bioreactor" includes a fermentation device consisting of one or more vessels and/or towers or piping arrangements, which includes the continuous stirred tank reactor (CSTR), an immobilised cell reactor, a gas-lift reactor, a bubble column reactor (BCR), a membrane reactor, such as a Hollow Fibre Membrane Bioreactor (HFMBR), a trickle bed reactor (TBR), monolith bioreactor, forced or pumped loop bioreactors or combinations thereof, or other vessel or other device suitable for gas-liquid contact.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "desired composition" is used to refer to the desired level and types of components in a substance, such as, for example, of a gas stream. More particularly, a gas is considered to have a "desired composition" if it contains a particular component (e.g. CO and/or $H_2$) and/or contains a particular component at a particular level and/or does not contain a particular component (e.g. a contaminant harmful to the micro-organisms) and/or does not contain a particular component at a particular level. More than one component may be considered when determining whether a gas stream has a desired composition.

The term "stream" is used to refer to a flow of material into, through and away from one or more stages of a process, for example, the material that is fed to a bioreactor and/or an optional $CO_2$ remover. The composition of the stream may vary as it passes through particular stages. For example, as a stream passes through the bioreactor, the CO content of the stream may decrease, while the $CO_2$ content may increase. Similarly, as the stream passes through the $CO_2$ remover stage, the $CO_2$ content will decrease.

Unless the context requires otherwise, the phrases "fermenting", "fermentation process" or "fermentation reaction" and the like, as used herein, are intended to encompass both the growth phase and product biosynthesis phase of the process.

The terms "increasing the efficiency", "increased efficiency" and the like, when used in relation to a fermentation process, include, but are not limited to, increasing one or more of: the rate of growth of micro-organisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of the fermentation, and further may reflect the value (which may be positive or negative) of any by-products generated during the process.

While certain embodiments of the invention, namely those that include the production of ethanol by anaerobic fermentation using CO and optionally H2 as the primary substrate, are readily recognized as being valuable improvements to technology of great interest today, it should be appreciated that the invention is applicable to production of alternative products such as other alcohols and the use of alternative substrates, particularly gaseous substrates, as will be known by persons of ordinary skill in the art to which the invention relates upon consideration of the instant disclosure. For example, gaseous substrates containing carbon dioxide and hydrogen may be used in particular embodiments of the invention. Further, the invention may be applicable to fermentations to produce acetate, butyrate, propionate, caproate, ethanol, propanol, and butanol, and hydrogen. By way of example, these products may be produced by fermentation using microbes from the genus *Moorella, Clostridia, Ruminococcus, Acetobacterium, Eubacterium, Butyribacterium, Oxobacter, Methanosarcina, Methanosarcina*, and *Desulfotomaculum*.

Gasification Process

The invention has particular applicability to supporting the production of products from syngas derived from gasification. In some embodiments of the invention, a feedstock is converted to syngas by gasification, and the syngas passed to a fermentation reaction where at least a portion of CO and/or H2 is converted to products, such as acid(s) and/or alcohol(s).

Gasification is a thermochemical process in which carbonaceous (carbon-rich) feedstocks such as coal, petcoke or biomass are converted into a gas comprising hydrogen and carbon monoxide (and lesser amounts of carbon dioxide and other trace gases) under oxygen limited, typically high pressure, high-heat and/or steam conditions. The resultant gas typically comprises mainly CO and $H_2$, with minimal volumes of $CO_2$, methane, ethylene and ethane. Gasification relies on chemical processes at elevated temperatures (typically <700° C.), whereby any carbon containing material is converted into syngas. Carbon containing feedstocks include coal, oil, petcoke, natural gas, biomass and organic waste such as municipal solid waste, sewage sludge or by-products of industrial processes, such as the paper pulping industry.

In the gasification process, the carbonaceous material undergoes several different processes including:
1. The pyrolysis (or devolatilization) process occurs as the carbonaceous particle heats up where volatiles are released and char is produced. The process is dependent on the properties of the carbonaceous material and determines the structure and composition of the char, which will then undergo gasification reactions.
2. The combustion process occurs as the volatile products and some of the char reacts with oxygen to form carbon dioxide and carbon monoxide, which provides heat for the subsequent gasification reactions.
3. Further production of gaseous products occurs as the char reacts with carbon dioxide and steam to produce carbon monoxide and hydrogen.
4. In addition, the reversible gas phase water gas shift reaction reaches equilibrium very fast at the temperatures in a gasifier. This balances the concentrations of carbon monoxide, steam, carbon dioxide and hydrogen in the resultant syngas stream exiting the gasifier.

Those skilled in the art will be aware of many gasification apparatus and/or systems suitable for the production of syngas. A summary of various gasification processes suitable for production of syngas are provided in Synthetic Fuels Handbook: Properties, Processes and Performance (J. Speight, McGraw-Hill Professional, 2008), which is incorporated herein by reference. Example gasification apparatus include counter-current fixed bed, co-current fixed bed, entrained flow, fluidised bed, plasma arc, single stage, multi stage gasifiers or combinations thereof.

Many design variations of gasifiers exist and are well known in the art, however they typically fall into three categories:

Moving Bed—Dry carbon fuel is fed through the top of the gasifier. As it slowly drops through the vessel, it reacts with steam and/or oxygen as they flow in opposite in directions over the bed. The fuel goes through the process until it is completely spent leaving behind low temperature syngas and molten ash. Trace contaminants are later scrubbed from the syngas.

Entrained Flow—Fuel can be fed dry or wet (mixed with water) into the gasifier. The reactants (steam and/or oxygen) flow uni-directionally up or down through the gasifier, as the stages of gasification take place, until high temperature completed syngas exits the top of the reactor. Molten slag drops out at the bottom.

Fluidized Bed—Steam and/or oxygen flow upwards through the reactor tower while fuel is injected into, and remains suspended in, this stream while gasification takes place. Moderate temperature syngas exits while dry (unmelted) ash is evacuated at the bottom.

Further examples of gasification processes to produce syngas are detailed in WO2008/006049 and WO2009/009388, both of which are fully incorporated herein by reference.

Syngas Conditioning

Particular embodiments of the invention include passing Syngas produced in a gasification process to a bioreactor, wherein it is contacted with one or more microorganisms and converted into products. The syngas stream produced in the gasification process typically contains small amounts of by-products, such as H2S, COS, NOx, BTEX (benzene, toluene, ethyl benzene and xylenes), tars and particulate matter. Such components can be removed using standard conditioning methodology in multiple unit operations. Those skilled in the art will be familiar with unit operations for removal of undesirable components. By way of example, BTEX components can be removed from the syngas stream by passing the stream through at (east one activated carbon bed. Furthermore, high efficiency Venturi scrubbing can be used to remove particulate matter and tars from a syngas stream (Benchmarking Biomass Gasification Technologies for Fuels, Chemicals Hydrogen Production; report prepared for US department of Energy and National Energy Technology Laboratory by Ciferno and Marano, 2002). Further examples of gas conditioning methods are detailed in WO2009/009388 and are incorporated herein by reference.

It is considered syngas passed to a fermentation bioreactor, in accordance with the methods of the invention, will require minimal conditioning, as most components are not considered to have a detrimental effect on the microbial culture. In particular embodiments of the invention, particulate matter and optionally tars are removed from the syngas stream using high efficiency Venturi scrubbing. Residual oxygen is optionally removed using a hot copper catalyst bed, prior to passing the syngas to the fermenter. Additionally or alternatively, oxygen can be reduced to water in the presence of hydrogen using other metal catalysts, such as palladium or platinum oxides.

Fermentation Reaction

Particular embodiments of the invention include the fermentation of a syngas substrate stream to produce products including alcohol(s) and optionally acid(s). Processes for the production of ethanol and other alcohols from gaseous substrates are known. Exemplary processes include those described for example in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Morella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp 41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited as Deposit Number 19630, on Oct. 19, 2007, at the German Resource Centre for Biological Material (DSMZ), located at Inhoffenstraβe 7B, Braunschweig, Germany, D-38124. In another embodiment, the *Clostridium autoethanogenum* is a *Clostridium autoethanogenum* having the identifying characteristics of DSMZ deposit number DSMZ 10061. Examples of fermentation of a substrate comprising CO to produce products including alcohols by *Clostridium autoethanogenum* are provided in WO2007/117157, WO2008/115080, WO2009/022925, WO2009/058028, WO2009/064200, WO2009/064201, WO2009/113878 and WO2009/151342 all of which are incorporated herein by reference.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (vi) J. L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor configured for gas/liquid contact wherein the substrate can be contacted with one or more microorganisms, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR), monolith bioreactor or loop reactors. Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is syngas derived from gasification. The syngas substrate will typically contain a major proportion of CO, such as at least about 15% to about 75% CO by volume, from 20% to 65% CO by volume, from 20% to 60% CO by volume, and from 20% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present. In particular embodiments, the presence of hydrogen results in an improved overall efficiency of alcohol production. The gaseous substrate may also contain some $CO_2$ for example, such as about 1% to about 80% $CO_2$ by volume, or 1% to about 30% $CO_2$ by volume.

In accordance with particular embodiments of the invention, the CO content and/or the H2 content of the substrate stream can be enriched prior to passing the stream to the bioreactor. For example, hydrogen can be enriched using technologies well known in the art, such as pressure swing adsorption, cryogenic separation and membrane separation. Similarly, CO can be enriched using technologies well known in the art, such as copper-ammonium scrubbing, cryogenic separation, COSORB™ technology (absorption into cuprous aluminium dichloride in toluene), vacuum swing adsorption and membrane separation. Other methods used in gas separation and enrichment are detailed in PCT/NZ2008/000275, which is fully incorporated herein by reference.

Additionally or alternatively, one or more particular components of the stream exiting the bioreactor can also be separated and/or enriched using such technologies. At least a portion of the enriched component(s), such as CH4 and/or CO2 can be diverted back to the gasifier to improve overall efficiency of the whole process. Additionally or alternatively, enriched component(s) such as CO and/or CO and/or H2 can be diverted back to the gasifier to improve efficiency of the fermentation stage.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemistry and Biotechnology Volume* 101, *Number* 3/October, 2002) could be used for this purpose.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/117157, WO2008/115080, WO2009/022925, WO2009/058028, WO2009/064200, WO2009/064201, WO2009/113878 and WO2009/151342 referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO2007/117157, WO2008/115080, WO2009/022925, WO2009/058028, WO2009/064200, WO2009/064201, WO2009/113878 and WO2009/151342 all of which are incorporated herein by reference.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO2007/117157, WO2008/115080, WO2009/022925, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously, introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which is produced as by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Stream Component Recycle

In accordance with the invention, there is provided a method of improving overall carbon capture efficiency and/or carbon capture of a fermentation process, the process including:
    conversion of a feedstock to syngas in a gasifier;
    passing the syngas to a bioreactor;
    fermenting at least a portion of the syngas in the bioreactor to produce products;
wherein components of the syngas not converted to products and/or by-products of the fermentation process exit the fermenter in an exit stream, wherein at least a portion of the exit stream is returned to the gasifier.

In particular embodiments, a syngas substrate is produced in a gasifier and at least a portion is passed to a bioreactor. The syngas substrate is contacted with one or more microorganisms and fermented to one or more products such as alcohols. During fermentation, by-products of fermentation such as $CO_2$ and/or components of the syngas stream not metabolised by the one or more microorganisms, exit the bioreactor in an exit stream. In accordance with the invention, at least a portion of the exit stream is passed to the gasifier. Additionally or alternatively, the exit stream comprises a first component and one or more second components, wherein at least a portion of the first component is separated from the one or more second components and passed to the gasifier.

In particular embodiments, syngas components, such as CO, H2 and optionally CO2 are converted into products, such as acid(s) and/or alcohol(s). In some embodiments, a microbial culture converts CO and optionally H2 into products including ethanol. The products can typically be recovered from the bioreactor in a product stream. In particular embodiments of the invention, the microbial culture is suspended in a liquid nutrient media. Accordingly, the products produced in the fermentation reaction can be recovered from a portion of the liquid nutrient media removed from the bioreactor in a product stream.

In some embodiments, the syngas substrate stream will typically be provided at a high flow rate and/or high pressure by sparging the stream into the bioreactor. As such, small amounts of product and/or water may be stripped from the liquid nutrient media in the bioreactor and carried into the exit stream. In particular embodiments, products stripped from the bioreactor can be separated from the exit stream by means well known in the art. For example, ethanol can be separated from the exit stream using existing membrane technologies. The separated product(s) can be combined with product(s) recovered from the fermentation broth by conventional means.

In accordance with particular methods of the invention, the syngas stream provided to the fermentation process contains carbon containing components such as CO2 and/or CH4 and/or BTEX and/or tars. Such components will not be converted to products by the microbial culture, and will thus exit the bioreactor in a typically gaseous exit stream. Furthermore, at least a portion of the CO and/or H2 components of the syngas stream fed into the bioreactor may not be converted into products by the microbial culture. Instead, at least a portion of the CO and/or H2 may exit the bioreactor in the exit stream. Furthermore In particular embodiments, the CO may be at least partially converted to CO2 by the microbial culture, particularly where H2 is provided in limiting concentrations. Accordingly, CO2 produced by the microbial culture may exit the bioreactor in the exit stream.

Thus, in accordance with the invention, at least a portion of one or more carbon containing exit stream components can be returned to the gasifier for conversion into syngas. In particular embodiments, the carbon containing components of the exit stream are selected from CO2, CH4 and/or other volatile organic compounds, tars, CO, BTEX, acids and alcohols. Additionally or alternatively, at least a portion of one or more of the hydrogen containing exit stream components are returned to the gasifier for conversion into syngas. In particular embodiments, the hydrogen containing components are selected from H2 and H2O.

Returning carbon containing component(s) from the exit stream to the gasifier reduces the amount of carbon from the feedstock required to produce syngas of a particular desired composition. Furthermore, returning hydrogen containing components from the exit stream to the gasifier reduces the amount of water/steam required to produce syngas of a particular desired composition. Accordingly, there will be an improvement in overall efficiency of the integrated process, and in particular embodiments, where syngas is converted to products such as acids and/or alcohols, the overall carbon capture of the process will increase.

In particular embodiments of the invention, the entire exit stream is diverted to the gasifier for conversion to syngas. In other embodiments, a portion of the exit stream is diverted to the gasifier for conversion into syngas. In particular embodiments, one or more components of the exit stream are separated from the exit stream and diverted to the gasifier. For example, CO2 and/or CH4 can be separated from the exit stream by separation methods well known in the art and returned to the gasifier for conversion into syngas. Other components can similarly be separated using techniques well known to those skilled in the art. Well known methods for gas separation and/or CO2 capture are detailed in PCT/NZ2008/000275 and are incorporated herein by reference.

Thus, in particular embodiments of the invention, there is provided a method of improving overall carbon capture in an integrated gasification-fermentation process, wherein at least a portion of syngas produced in a gasification stage is passed to a bioreactor, wherein one or more micro-organisms convert at least a portion of the syngas to products, such as alcohols, in a fermentation stage. In particular embodiments, by-products produced in the fermentation step, such as CO2 exit the bioreactor in an exit stream, wherein at least a portion of the exit stream is passed to the gasification stage.

In another embodiment, components such as BTEX and/or tars may be desirably removed from the syngas stream prior to the stream passing to the bioreactor. In such embodiments, the components, such as BTEX and/or tars can be separated using methods well known in the art and returned to the gasifier for conversion into syngas. As such, in particular embodiments, there is provided a method of improving overall efficiency and/or carbon capture of a fermentation process, the process including:
 conversion of a feedstock to syngas in a gasifier;
 passing the at least a portion of the syngas to a bioreactor;
 fermenting at least a portion of the syngas in the bioreactor to produce products;
wherein the method includes separating one or more components of the syngas prior to passing the syngas to the bioreactor, and diverting the one or more components to the gasifier.

By way of example, components such as H2S, CO2, tars and/or BTEX can be removed from the syngas substrate stream prior to passing to the bioreactor. Such components can be removed using standard separation technology, such as solvent separation. Examples of such separation methods are detailed in Gas Purification 5ed. (Kohl, A., Nielsen, R., Gulf Publishing Company, 1997). For example, acid gases, such as H2S and/or CO2 can be removed from a gas stream using the Selexol™ process (www.uop.com/objects/97%20selexol.pdf accessed 23 Mar. 2008). The separated components can then be recovered and optionally returned to the gasifier.

General

Embodiments of the invention are described by way of example. However, it should be appreciated that particular steps or stages necessary in one embodiment may not be necessary in another. Conversely, steps or stages included in the description of a particular embodiment can be optionally advantageously utilised in embodiments where they are not specifically mentioned.

While the invention is broadly described with reference to any type of stream that may be moved through or around the system(s) by any known transfer means, in certain embodiments, the substrate and/or exhaust streams are gaseous. Those skilled in the art will appreciate that particular stages may be coupled by suitable conduit means or the like, configurable to receive or pass streams throughout a system. A pump or compressor may be provided to facilitate delivery of the streams to particular stages. Furthermore, a compressor can be used to increase the pressure of gas provided to one or more stages, for example the bioreactor. As discussed hereinabove, the pressure of gases within a bioreactor can affect the efficiency of the fermentation reaction performed therein.

Thus, the pressure can be adjusted to improve the efficiency of the fermentation. Suitable pressures for common reactions are known in the art.

In addition, the systems or processes of the invention may optionally include means for regulating and/or controlling other parameters to improve overall efficiency of the process. For example particular embodiments may include determining means to monitor the composition of substrate and/or exhaust stream(s). In addition, particular embodiments may include a means for controlling the delivery of substrate stream(s) to particular stages or elements within a particular system if the determining means determines the stream has a composition suitable for a particular stage. For example, in instances where a gaseous substrate stream contains low levels of CO or high levels of $O_2$ that may be detrimental to a fermentation reaction, the substrate stream may be diverted away from the bioreactor. In particular embodiments of the invention, the system includes means for monitoring and controlling the destination of a substrate stream and/or the flow rate, such that a stream with a desired or suitable composition can be delivered to a particular stage.

In addition, it may be necessary to heat or cool particular system components or substrate stream(s) prior to or during one or more stages in the process. In such instances, known heating or cooling means may be used.

Figure 1:
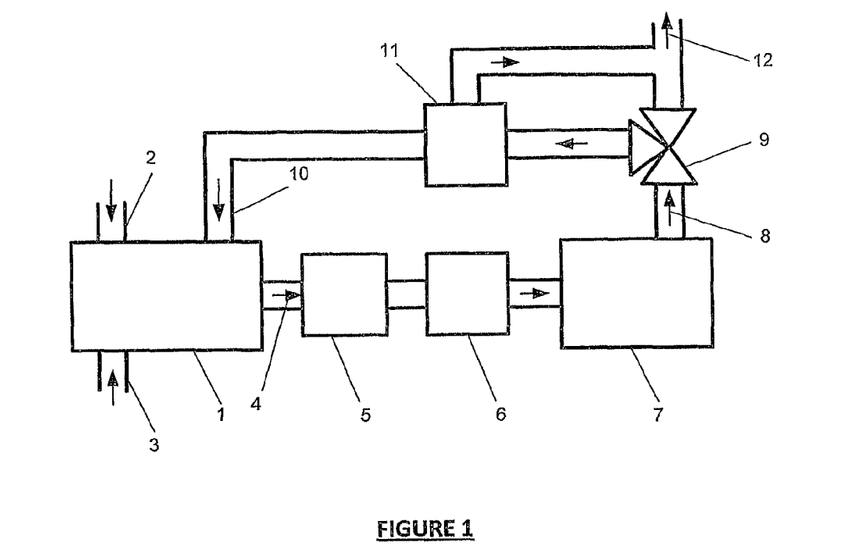
FIG. 1: is a schematic representation of a system including means for returning an exit stream from a fermenter to a gasifier.

FIG. 1 is a schematic representation of a system 101 according to one embodiment of the invention. Carbonaceous feedstock, such as biomass, is fed into gasifier 1, via inlet port 2. A steam and/or oxygen stream is supplied to gasifier 1, via inlet port 3. In particular embodiments of the invention, the gasifier is configured such that the feedstock stream and steam and/or oxygen react to produce syngas. In particular embodiments, the syngas produced in accordance with the methods of the invention is produced at substantially constant composition during steady state operation.

The syngas exits the gasifier 1 through exit port 4 and passes to optional syngas conditioning stage 5 before passing to bioreactor 7, via optional pretreat 6. In particular embodiments, optional syngas conditioning stage 5 is configured to remove components of the syngas stream that may be detrimental to a microbial culture, such as oxygen, particulate matter, tars, H2S and/or BTEX. In particular embodiments, at least a portion of the removed components can be returned to the gasifier 1.

Pre-treat 6 may be used to control various aspects of the stream, including temperature and levels of contaminants or other undesired components or constituents. It may also be used to add components to the stream. This will depend on the particular composition of the syngas stream and/or the particular fermentation reaction and/or the micro-organisms selected therefor.

Pre-treat 6 may be positioned elsewhere within system 101 or may be omitted, or multiple pre-treats 6 may be provided at various points in system 101. This will depend on the particular source of the syngas stream and/or the particular fermentation reaction and/or the micro-organisms selected therefor.

Following optional pre-treatment the syngas substrate stream may be passed to bioreactor 7 by any known transfer means. Bioreactor 7 is configured to perform the desired fermentation reaction to produce products. According to certain embodiments, bioreactor 7 is configured to process a CO and H2 containing substrate so as to produce one or more acids and/or one or more alcohols by microbial fermentation. In a particular embodiment, bioreactor 7 is used to produce ethanol and/or butanol. Bioreactor 7 may comprise more than one tank, each tank being configured to perform the same reaction and/or different stages within a particular fermentation process and/or different reactions, including different reactions for different fermentation processes which may include one or more common stages.

Bioreactor 7 may be provided with cooling means for controlling the temperature therein within acceptable limits for the micro-organisms used in the particular fermentation reaction to be performed.

A pump or compressor (not shown) may be provided upstream of bioreactor 7 so that the pressure of gas within bioreactor 7 is increased. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

The products produced in the bioreactor 7 may be recovered by any recovery process known in the art. An exit stream, comprising components such as unconverted CO and/or H2, CO2, CH4, BTEX, tars, and/or products stripped from the bioreactor exits bioreactor 7 via outlet port 8. Valve 9 is configured to pass at least a portion of the exit stream back to gasifier 1, via inlet port 10. Prior to returning to the gasifier 1, the exit stream may be conditioned or particular components enriched in optional gas treatment stage 11. In particular embodiments, optional gas treatment stage 11 is configured to remove undesirable components. Additionally or alternatively, optional gas treatment stage 11 is configured to enrich particular components, such as CO2, and pass the enriched stream to gasifier 1. Unwanted components can be returned to port 12 for disposal.

Means for determining the composition of the stream may be optionally included at any stage of the system. Such means can be associated with diverting means such that streams with particular compositions can be diverted to or away from particular stages if necessary or as desired. Means for diverting and/or transferring the streams around the various stages of the system will be known to those skilled in the art.

Example 1

| Solution A | | | |
|---|---|---|---|
| $NH_4Ac$ | 3.083 g | $CaCl_2 \cdot 2H_2O$ | 0.294 g |
| $MgCl_2 \cdot 6H_2O$ | 0.61 g | KCl | 0.15 g |
| Distilled Water | | Up to 1 L | |

| Component/0.1M solution (aq) | Quantity/ml into 1 L media | Component/0.1M solution (aq) | Quantity/ml into 1 L media |
|---|---|---|---|
| Solution B | | | |
| $FeCl_3$ | 10 ml | $Na_2SeO_3$ | 1 ml |
| $CoCl_2$ | 5 ml | $Na_2MoO_4$ | 1 ml |
| $NiCl_2$ | 5 ml | $ZnCl_2$ | 1 ml |
| $H_3BO_3$ | 1 ml | MnCl2 | 1 mL |
| Solution C | | | |
| Biotin | 20.0 mg | Nicotinic acid | 50.0 mg |
| Folic acid | 20.0 mg | Calcium D-(*)-pantothenate | 50.0 mg |
| Pyridoxine. HCl | 10.0 mg | Vitamin B12 | 50.0 mg |
| Thiamine. HCl | 50.0 mg | p-Aminobenzoic acid | 50.0 mg |
| Riboflavin | 50.0 mg | Thioctic acid | 50.0 mg |
| Distilled water | | To 1 Litre | |

Preparation of Cr (II) Solution

A 1 L three necked flask was fitted with a gas tight inlet and outlet to allow working under inert gas and subsequent transfer of the desired product into a suitable storage flask. The flask was charged with $CrCl_3.6H_2O$ (40 g, 0.15 mol), zinc granules [20 mesh] (18.3 g, 0.28 mol), mercury (13.55 g, 1 mL, 0.0676 mol) and 500 mL of distilled water. Following flushing with $N_2$ for one hour, the mixture was warmed to about 80° C. to initiate the reaction. Following two hours of stirring under a constant $N_2$ flow, the mixture was cooled to room temperature and continuously stirred for another 48 hours by which time the reaction mixture had turned to a deep blue solution. The solution was transferred into $N_2$ purged serum bottles and stored in the fridge for future use.

Bacteria: *Clostridium autoethanogenum* used is that deposited at the German Resource Centre for Biological Material (DSMZ) and allocated the accession number DSMZ 19630.

Sampling and Analytical Procedures

Media samples were taken from the CSTR reactor at intervals over periods up to 20 days. Each time the media was sampled care was taken to ensure that no gas was allowed to enter into or escape from the reactor.

HPLC:

HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

Method for Sample Preparation:

400 μL of sample and 50 μL of 0.15M $ZnSO_4$ and 50 μL of 0.15M $Ba(OH)_2$ are loaded into an Eppendorf tube. The tubes are centrifuged for 10 min. at 12,000 rpm, 4° C. 200 of the supernatant are transferred into an HPLC vial, and 5 μL are injected into the HPLC instrument.

Headspace Analysis:

Measurements were carried out on a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Substrate

Bottled synthesis gas was obtained from Range Fuels two dry ton/day demonstration facility in Denver Colo. (USA). The feedstock was chipped Colorado Pine and the derived syngas was dried and substantially stripped of residual aromatics and excess CO2 prior to bottling.

Example 1

Batch Fermentation in CSTR

Liquid medium (800 mL) containing solution A was aseptically and anaerobically transferred into a 1 L CSTR vessel, and continuously sparged with $N_2$. Once transferred, the reduction state and pH of the medium could be measured directly via probes. The medium was heated to 37° C. and stirred at 400 rpm. Phosphoric acid (30 mM), sodium tungstate (10 μM), solution B and solution C were then added. Sodium sulfide solution (0.5 mM) was added to the fermentation vessel, with the medium then reduced to −200 mV by addition of a chromium (II) chloride solution.

Prior to inoculation, the $N_2$ gas was switched to a gas blend of 30% CO, 50% $H_2$, 5% $CO_2$ and 15% $CH_4$ (Range Fuels synthesis gas), which was continuously sparged into the fermentation broth throughout the experiment. An actively growing *Clostridium autoethanogenum* culture was inoculated into the CSTR at a volume of approximately 10% (v/v). Substrate and agitation was increased over time in accordance with the growth of the microbial culture.

Figure 2:
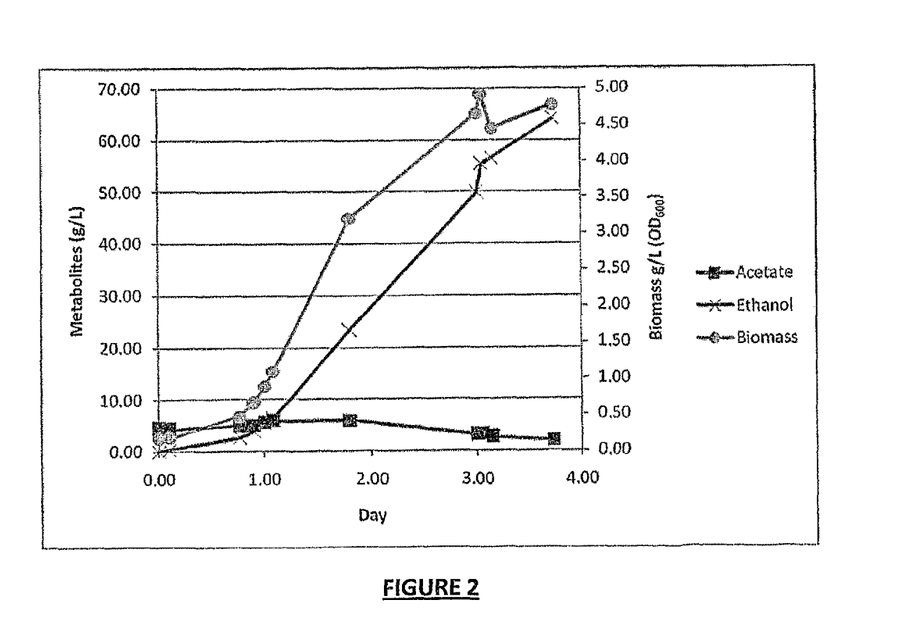
FIG. 2: shows metabolite production and microbial growth over time in the fermentation of Example 1.

Results:

Metabolite production and microbial growth can be seen in FIG. 2. From day 1, biomass and ethanol production commenced, initially following an exponential trend, before conforming to a more linear rate of production. Biomass reached a peak of 4.9 g/L at day 3 and ethanol concentration increased to a maximum of 64 g/L at day 3.7. Acetate accumulated to 5.9 g/L before dropping to 2 g/L by the end of the fermentation.

Figure 3:
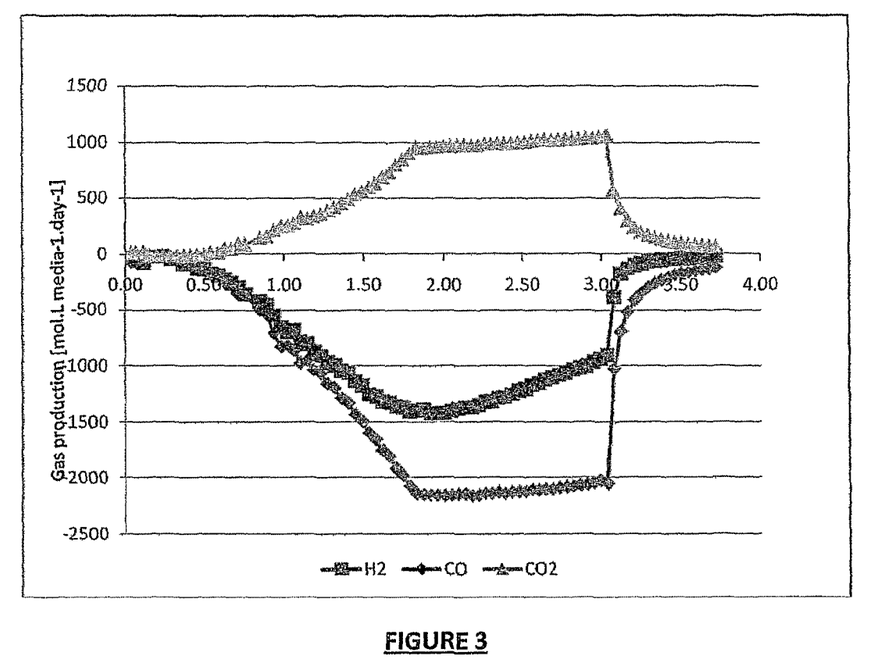
FIG. 3: shows gas consumption and production over time for the fermentation of Example 1.

Gas consumption and production trends can be seen in FIG. 3. As the culture began to grow post inoculation, increasingly higher agitation and gas flow was provided to the fermentation broth. This resulted in stable CO consumption of more than 2.0 mol/L/day between days 1.8 and 3.0, during which the highest rate of ethanol production was observed. $H_2$ consumption reached a maximum of 1.4 mol/L/day at day 2 of this fermentation run, with a combined (CO and $H_2$) peak gas consumption rate of 3.6 g/L/d. As the microbial culture consumed CO, $CO_2$ was produced up to a peak of approximately 1.0 mol/L/d between days 1.8 and 3.0.

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, heading, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What I claimed is:

1. A method of increasing carbon capture in a fermentation process, the method comprising gasifying a feedstock in a gasifier to produce a syngas stream and contacting at least a portion of the syngas stream with at least one microorganism in a bioreactor at fermentation conditions to produce at least one product, wherein at least a portion of an exit stream comprising carbon dioxide that exits the bioreactor is passed into the gasifier.

2. The method of claim 1, wherein carbon dioxide is substantially separated from one or more other components in the exit stream.

3. The method of claim 1, wherein the exit stream comprises at least one component of the syngas stream not converted to products by fermentation.

4. The method of claim 3, wherein the component not converted to products is methane.

5. The method of claim 4, wherein at least a portion of the methane exiting the bioreactor is directed to the gasifier.

6. The method of claim 4, wherein methane is substantially separated from at least one component in the exit stream.

7. The method of claim 1, wherein the microorganism is an anaerobic carboxydotrophic bacterium.

8. The method of claim 7, wherein the carboxydotrophic bacterium is selected from the group consisting of *Clostridium, Moorella, Pyrococcus, Eubacterium, Desulfobacterium, Carboxydothermus, Acetogenium, Acetobacterium, Acetoanaerobium, Butyribaceterium* and *Peptostreptococcus*.

9. The method of claim 8, wherein the carboxydotrophic bacterium is *Clostridium autoethanogenum*.

10. The method of claim 9, wherein the *Clostridium autoethanogenum* is *Clostridium autoethanogenum* having the identifying characteristics of the strain deposited at the German Resource Centre for Biological Material (DSMZ) under the identifying deposit number 19630.

11. The method of claim 1, wherein the at least one product comprises at least one acid, at least one alcohol and mixtures thereof.

12. The method of claim 11, wherein the at least one acid comprises acetate.

13. The method of claim 11, wherein the at least one alcohol comprises ethanol.

* * * * *